United States Patent
White et al.

(10) Patent No.: US 9,157,852 B2
(45) Date of Patent: Oct. 13, 2015

(54) EXPLOSIVE MATERIAL DETECTION

(71) Applicant: Raytheon Company, Waltham, MA (US)

(72) Inventors: Jack E. White, Santa Barbara, CA (US); Kenneth W. Brown, Yucaipa, CA (US); Steven L. Kaufman, Port Hueneme, CA (US)

(73) Assignee: RAYTHEON COMPANY, Waltham, MA (US)

( * ) Notice: Subject to any disclaimer, the term of this patent is extended or adjusted under 35 U.S.C. 154(b) by 0 days.

(21) Appl. No.: 13/961,168

(22) Filed: Aug. 7, 2013

(65) Prior Publication Data

US 2015/0160181 A1    Jun. 11, 2015

Related U.S. Application Data

(63) Continuation-in-part of application No. 12/884,428, filed on Sep. 17, 2010, now abandoned.

(51) Int. Cl.
*G06F 19/00* (2011.01)
*G01N 21/3581* (2014.01)
(Continued)

(52) U.S. Cl.
CPC ............ *G01N 21/3581* (2013.01); *G01N 21/62* (2013.01); *G01N 21/636* (2013.01); *G01N 22/00* (2013.01); *G01N 33/227* (2013.01); *G01S 7/411* (2013.01); *G01S 7/412* (2013.01);
(Continued)

(58) Field of Classification Search
CPC .............. G01N 21/3581; G01N 21/62; G01N 21/3563; G01N 22/00; G01S 7/411; G01S 7/024; G01S 7/412; G01S 7/414; G01S 7/415; G01S 13/04; G01S 13/34; G01S 13/66; G01S 13/865; G01S 13/867; G01S 13/887; G01V 8/005; G01J 3/42
USPC ............... 702/22, 23, 30, 38, 73, 74, 75, 104, 702/106, 159, 189; 250/282, 338.1, 341.1, 250/341.8, 358.1, 472.1; 324/309; 342/52; 455/11; 136/246
See application file for complete search history.

(56) References Cited

U.S. PATENT DOCUMENTS 3,384,749 A   5/1968   Golay
5,449,909 A   9/1995   Kaiser et al.
(Continued)

FOREIGN PATENT DOCUMENTS

WO    2009131808 A2    10/2009

OTHER PUBLICATIONS

Furstenberg, et al., "Stand-Off Detection of Trace Explosives by Infrared Photo-Thermal Spectroscopy," Technologies for Homeland Security, HSZT '09, IEEE Conference, May 11, 2009, pp. 465-471.
(Continued)

*Primary Examiner* — John H Le
(74) *Attorney, Agent, or Firm* — Burns & Levinson LLP; Joseph M. Maraia

(57) ABSTRACT

A system for detecting explosive materials. The system includes radiated high power electromagnetic radiation at one or more frequencies in the millimeter wave spectrum or above to interact with a sample and be reflected therefrom. The system also includes at least one electromagnetic sensor to measure emissions at harmonic frequencies and characteristics unique to one or more explosive materials. The system also includes a processor to collate and maintain a lookup table to identify specific explosive material types.

16 Claims, 4 Drawing Sheets

(51) Int. Cl.
*G01S 7/41* (2006.01)
*G01V 8/00* (2006.01)
*G01N 21/63* (2006.01)
*G01S 13/88* (2006.01)
*G01N 22/00* (2006.01)
*G01N 33/22* (2006.01)
*G01N 21/62* (2006.01)
*G01N 21/17* (2006.01)

(52) U.S. Cl.
CPC .............. *G01S 13/887* (2013.01); *G01V 8/005* (2013.01); *G01N 2021/1793* (2013.01)

(56) References Cited

U.S. PATENT DOCUMENTS

| | | | |
|---|---|---|---|
| 5,710,430 | A | 1/1998 | Nuss |
| 6,078,047 | A | 6/2000 | Mittleman et al. |
| 6,909,095 | B2 | 6/2005 | Tran et al. |
| 7,639,178 | B1 | 12/2009 | Mulbrook et al. |
| 7,645,069 | B1 | 1/2010 | Fine et al. |
| 7,745,792 | B2 | 6/2010 | Breit et al. |
| 7,795,583 | B1 | 9/2010 | Hubbard et al. |
| 2004/0051867 | A1 | 3/2004 | Brestel et al. |
| 2006/0022140 | A1 | 2/2006 | Connelly et al. |
| 2006/0111619 | A1 | 5/2006 | Catiglione et al. |
| 2006/0255277 | A1* | 11/2006 | Cole et al. .................. 250/341.1 |
| 2007/0075246 | A1 | 4/2007 | Gatt |
| 2008/0129581 | A1* | 6/2008 | Douglass et al. ............... 342/52 |
| 2008/0203306 | A1 | 8/2008 | Zhang et al. |
| 2009/0045343 | A1 | 2/2009 | Breit et al. |
| 2009/0272424 | A1* | 11/2009 | Ortabasi ....................... 136/246 |
| 2010/0282960 | A1 | 11/2010 | Clark |
| 2011/0059688 | A1 | 3/2011 | Noonan et al. |
| 2012/0072127 | A1 | 3/2012 | White et al. |
| 2012/0161762 | A1 | 6/2012 | Zank et al. |
| 2013/0063299 | A1 | 3/2013 | Proudkii |

OTHER PUBLICATIONS

Doyle et al., Stand-Off Detection of Hidden Threat Objects on Personnel at Checkpoints and in Public Areas Using Active Millimetre-Wave Imaging: Passive Millimetre-Wave and Terahertz Imaging and Technology; proceedings of the SPIE; vol. 5619; pp. 90-97, Jan. 1, 2004.

Hubbard et al., Long-Range Thermal Imaging using a Millimeter-Wave source; The 33rd IEEE International Conference on Plasma Science; IEEE conference record—Abstracts; p. 352, Jan. 1, 2006.

Andrews, et al., Detection of Concealed Explosuves at Stand-Off Distances Using Wide Band Swept Millimetre Waves; Millimetre Wave and Terahertz Sensors and Technology; Proceedings of the SPIE; vol. 7117; Oct. 2, 2008.

Kuznetsov et al., "Combined Sensor for Detection of Explosives Based on Timed Neutron Source and Continuous Microwaves," Proc. of the 5th international symposium on Technology and the Mine Problem, Monterey, CA, USA, Apr. 21-25, 2002, 12 pages.

* cited by examiner

EXPLOSIVE MATERIAL DETECTION

RELATED APPLICATION

The present application is a continuation-in-part of U.S. patent application Ser. No. 12/884,428, filed on Sep. 17, 2010. The entire content of the above applications is incorporated herein by reference.

GOVERNMENT SUPPORT

This disclosure was supported, in whole or in part, by Contract No. DHS, BAA 09-04, Co #78440-001-10, awarded by the Department of Defense. The Government may have certain rights in the disclosure.

FIELD OF THE INVENTION

The currently described invention relates to systems and methods for detecting explosive materials.

BACKGROUND

Prior art methods for detecting explosive materials typically involve exciting a sample by physically contacting the sample with an ultrasound excitation source. A temperature sensor is typically used to monitor the thermal properties of the excited sample to determine if the sample material is an explosive material. These methods do not adequately distinguish between explosive materials and non-explosive materials.

A need therefore exists for improved systems and methods for detecting and classifying explosive materials at standoff ranges.

SUMMARY

Embodiments described herein relate generally to systems and methods for detecting explosives.

In one aspect, at least one embodiment described herein provides a system for detecting explosive materials. The system includes at least one high power electromagnetic transmitter configured to radiate a sample with high power electromagnetic radiation. The system also includes at least one electromagnetic sensor configured to detect one or more non-linear electromagnetic reflections. The one or more non-linear electromagnetic reflections have a harmonic frequency corresponding to one or more harmonic frequencies of the radiated high power electromagnetic radiation. The non-linear electromagnetic reflections are reflected by the sample in response to the radiated high power electromagnetic radiation. The system also includes a processor configured to control at least one characteristic of the radiated high power electromagnetic radiation. The processor is also configured to process the detected one or more non-linear electromagnetic reflections having a harmonic frequency to identify a match between the detected one or more non-linear electromagnetic reflections having a harmonic frequency and one or more harmonic reflections associated with at least one explosive material. The processor, upon identifying the match, is also configured indicate detection of an explosive material. The processor is also configured to indicate a type of the detected explosive material.

Any of the aspects and/or embodiments described herein can include one or more of the following embodiments. In some embodiments, the processor collates and catalogs the detected one or more non-linear electromagnetic reflections having a harmonic frequency reflected by the sample. In some embodiments, the one or more non-linear electromagnetic reflections having a harmonic frequency are caused by a non-linear response to the radiated high power electromagnetic radiation interacting with the sample. In some embodiments, the high power electromagnetic transmitter radiates the high power electromagnetic radiation at one or more of millimeter wave frequencies, W-band frequencies, or Ka-band frequencies. In some embodiments, the high power electromagnetic transmitter radiates the high power electromagnetic radiation at a power density level configured to minimize penetration depth of the high power electromagnetic radiation into the sample and cause the high power electromagnetic radiation to reflect off of the sample non-linearly, producing the one or more non-linear electromagnetic reflections having the harmonic frequency corresponding to the one or more harmonic frequencies of the radiated high power electromagnetic radiation. In some embodiments, the power density level is also configured to avoid ignition or detonation of the sample. In some embodiments, the high power electromagnetic transmitter radiates the high power electromagnetic radiation at a power density of at least 10 Watts/cm$^2$.

In some embodiments, millimeter wave frequencies, terahertz-band frequencies, or a combination of both are detected by the at least one electromagnetic sensor. In some embodiments, each of a plurality of the electromagnetic sensors is configured to detect any of the one or more non-linear electromagnetic reflections having a specific harmonic frequency of the radiated high power electromagnetic radiation. In some embodiments, the processor is configured to identify the match between the detected one or more non-linear electromagnetic reflections having the harmonic frequency and the reflective harmonic characteristics of the at least one explosive material by comparing a relative amplitude of the detected one or more non-linear electromagnetic reflections having the harmonic frequency with a relative amplitude of the one or more harmonic reflections associated with the at least one explosive material. In some embodiments, the type of the detected explosive material is at least one of HMX, Trinitrotoluene (TNT), C-4, Semtex, or Ammonium Nitrate.

In one aspect, at least one embodiment described herein provides a method for detecting explosive materials. The method includes radiating a sample with high power electromagnetic radiation using at least one high power electromagnetic transmitter. The method also includes detecting, using one or more electromagnetic sensors, one or more non-linear electromagnetic reflections having a harmonic frequency corresponding to one or more harmonic frequencies of the radiated high power electromagnetic radiation. The non-linear electromagnetic reflections are reflected by the sample in response to the radiated high power electromagnetic radiation. The method also includes controlling, by a processor, at least one characteristic of the radiated high power electromagnetic radiation. The method also includes identifying, by the processor, a match between the detected one or more non-linear electromagnetic reflections having a harmonic frequency and one or more harmonic reflections associated with at least one explosive material. The processor, upon identifying the match, is configured indicate detection of an explosive material. The processor is also configured to indicate a type of the detected explosive material.

Any of the aspects and/or embodiments described herein can include one or more of the following embodiments. In some embodiments, the processor collates and catalogs the detected one or more non-linear electromagnetic reflections having a harmonic frequency reflected by the sample. In some embodiments, one or more of millimeter wave frequencies, W-band frequencies, or Ka-band frequencies are radiated by the high power electromagnetic transmitter. In some embodiments, millimeter wave frequencies, terahertz-band frequencies, or a combination of both, are detected by the at least one electromagnetic sensor.

In some embodiments, the step of identifying is performed by comparing a relative amplitude of the detected one or more non-linear electromagnetic reflections having the harmonic frequency with a relative amplitude of the one or more harmonic reflections associated with the at least one explosive material. In some embodiments, the method includes using each of a plurality of the electromagnetic sensors to detect any of the one or more non-linear electromagnetic reflections having a specific harmonic frequency of the radiated high power electromagnetic radiation. In some embodiments, the at least one characteristic includes at least one of a power of the radiated high power electromagnetic radiation or a frequency of the radiated high power electromagnetic radiation.

Other aspects and advantages of the current invention will become apparent from the following detailed description, taken in conjunction with the accompanying drawings, illustrating the principles of the invention by way of example only.

BRIEF DESCRIPTION OF THE DRAWINGS

The foregoing features of various embodiments of the invention will be more readily understood by reference to the following detailed descriptions in the accompanying drawings, in which.

DETAILED DESCRIPTION OF ILLUSTRATIVE EMBODIMENTS

Figure 1:
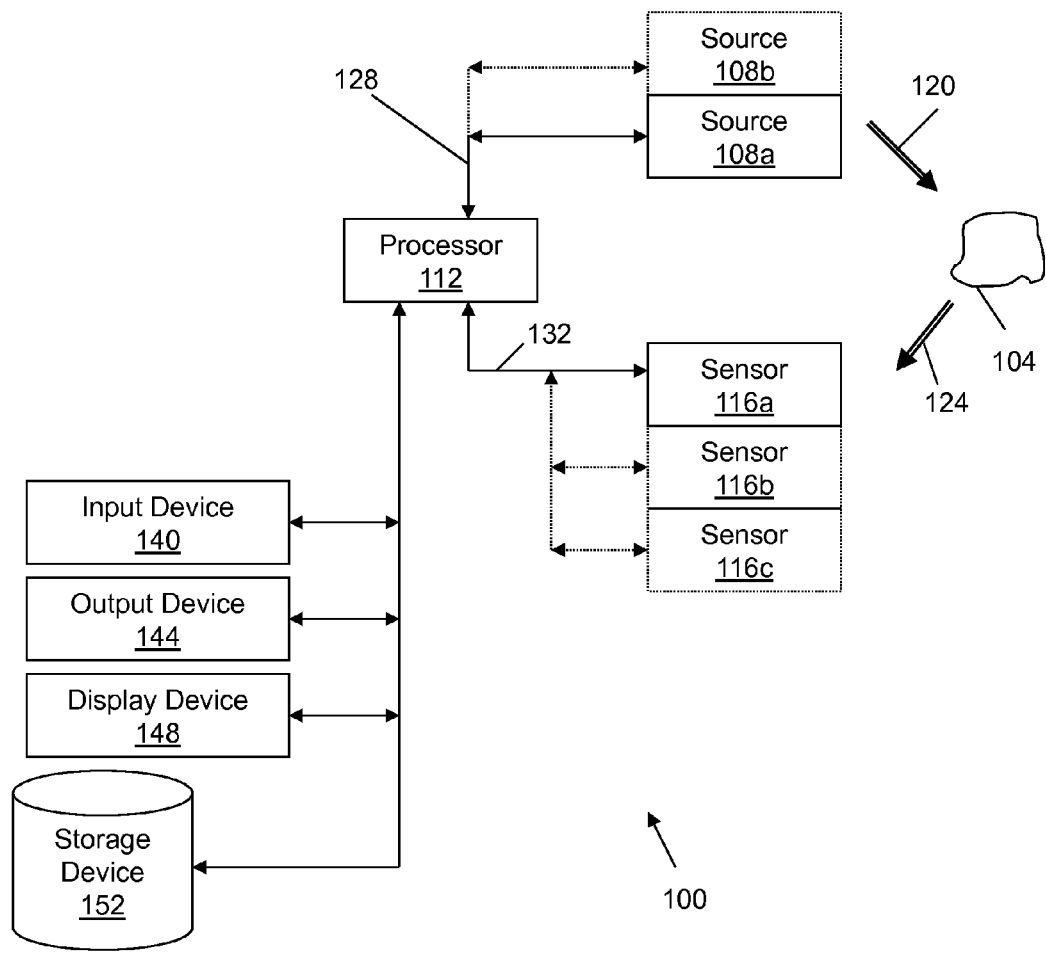
FIG. 1 is schematic illustration of a system for detecting explosive materials, according to an illustrative embodiment.

FIG. 1 is a schematic illustration of system 100 for detecting and classifying explosive materials, according to various embodiments. The system 100 includes a processor 112 that is coupled (e.g., digitally coupled) to at least one high power electromagnetic transmitter 108a (generally 108) for radiating high power electromagnetic radiation 120 and includes at least one electromagnetic sensor 116a (generally 116) to detect one or more non-linear electromagnetic reflections 124 having a harmonic frequency corresponding to one or more harmonic frequencies of the high power electromagnetic radiation 120.

The high power electromagnetic transmitter 108 radiates high power electromagnetic radiation 120 to interact with a sample 104. Generally, an electromagnetic transmitter is considered a high power electromagnetic transmitter 108 if the transmitter is capable of generating over 100 watts (W) of average power. However, high power electromagnetic transmitter 108 as used herein will be understood to also include any transmitter capable of radiating a sample of interest with an incident power density (i.e., power density at the site of interaction with the sample 104) of at least 10 W/cm$^2$.

In various embodiments, the high power electromagnetic transmitter 108 advantageously radiates electromagnetic radiation 120 at millimeter wave (mmW), W-band, and/or Ka-band frequencies. Millimeter wave frequencies are generally considered to be between 30-300 GHz. W-band frequencies are generally considered to be frequencies between 75-110 GHz. Ka-band frequencies are generally considered to be frequencies between 26.5-40 GHz. Frequencies lower than these frequencies will generally penetrate too deeply into the sample 104 and will not produce the non-linear electromagnetic reflections 124. Such lower frequencies only generate linear electromagnetic reflections (i.e., reflections at the same frequency as the radiated high power electromagnetic radiation 120). Frequencies higher than mmW, W-band, or Ka-band can cause the non-linear electromagnetic reflections 124. However, generating sufficient power at such higher frequencies generally requires more complex, expensive equipment.

In various embodiments, high power electromagnetic transmitter 108 radiates a combination of frequencies that includes both W-band and Ka-band emissions. In various embodiments, the system includes multiple high power electromagnetic transmitters (e.g., high power electromagnetic transmitters 108a and 108b). In various embodiments, each of the multiple high power electromagnetic transmitters radiates electromagnetic radiation in either W band and/or Ka band. In various embodiments, a single high power electromagnetic transmitter 108 radiates electromagnetic radiation in one specific frequency. In various embodiments, the high power electromagnetic transmitter is a GaN-based multi-element array.

In accordance with various embodiments, the non-linear electromagnetic reflections 124 are produced when the high power electromagnetic transmitter 108 radiates high power electromagnetic radiation 120 having a sufficient incident power density (i.e., power density at the site of interaction with the sample 104). If the incident power density is too low, the sample 104 will produce only linear reflections and the non-linear electromagnetic reflections 124 will not be generated. In contrast, if the power density is too high, the sample 104 (e.g., an explosive such as HMX, Trinitrotoluene, C-4, Semtex, or Ammonium Nitrate) will ignite. In various embodiments, an incident power density of 10 W/cm$^2$ or greater generates non-linear electromagnetic reflections 124. In various embodiments, a power density in excess of 100 W/cm$^2$ increases a risk of ignition of the sample 104.

The incident power density (PD) at the sample 104 depends on four factors: 1) the radiated power (Pt) of the high power electromagnetic transmitter 108; 2) the size (D) of the radiating antenna; 3) The distance or range (R) from the antenna to the sample; and 4) the wavelength ($\lambda$) of the radiated high power electromagnetic radiation 120. These factors are approximately related by PD=(D*Pt)/(R*$\lambda$). Therefore, larger radiating antennae and higher radiated power result in increased incident power density. However, increased range between the system 100 and the sample 104 and increased wavelength (i.e., lower frequency of the radiated high power electromagnetic radiation 120) result in decreased incident power density.

Accordingly, system 100 can be effective at any range so long as the high power electromagnetic transmitter 108 is capable of offsetting the increased range with increased antenna size and increased radiated power. However, such increased antenna size and increased radiated power result in increased complexity and cost of the system 100. In accordance with various embodiments, the system 100 can be designed to produce sufficient incident power density at a standoff range (i.e., the range at which the system 100 will not be damaged by detonation of the sample 104). In various embodiments, the high power electromagnetic transmitter 108 can be located at various ranges relative to the sample 104. In various embodiments, the output power of the high power electromagnetic transmitter 108 is variable and the processor 112 controls the electromagnetic transmitter 108 to provide the best detection capability.

Frequency of the radiated high power electromagnetic radiation 120 also affects the penetration depth of the high power electromagnetic radiation 120 into the sample 104. Lower frequencies generally penetrate deeper into the sample and thus require greater incident power density in order to produce non-linear electromagnetic reflections 124 because the power must be distributed over a greater volume of sample 104. Therefore, in various embodiments, it is desirable to operate the system 100 by selecting W-band radiation that minimizes the penetration depth of electromagnetic radiation 120 into the sample 104. In various embodiments, W-band radiation is selected so that the radiated penetration is to a depth of 1 mm or less. In various embodiments, use of W-band radiation results in a radiated penetration depth of less than about 0.020 inches (0.508 mm).

The electromagnetic sensor(s) 116 detect non-linear electromagnetic reflections 124, reflected by the sample 104 in response to the radiated high power electromagnetic radiation 120 interacting non-linearly with the sample 104. The non-linear electromagnetic reflections 124 include reflections having at least one harmonic frequency corresponding to one or more harmonic frequencies of the high power electromagnetic radiation 120. The system 100 discerns the type of material in the sample 104 (e.g., type of explosive material) based on the relative amplitude of the reflected harmonics from the sample (sample reflections 124). In accordance with various embodiments, the radiated electromagnetic radiation (electromagnetic radiation 120) will be at a fundamental frequency relative to the harmonic frequencies of the non-linear electromagnetic reflections 124.

Figure 3:
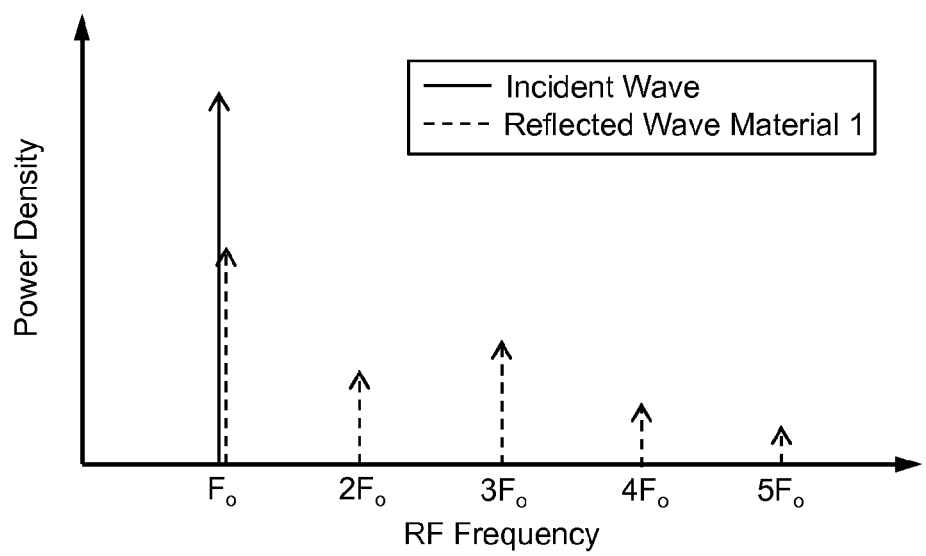
FIG. 3 is the relative amplitude vs. frequency of the incident and reflected electromagnetic waveforms for material #1.
Figure 4:
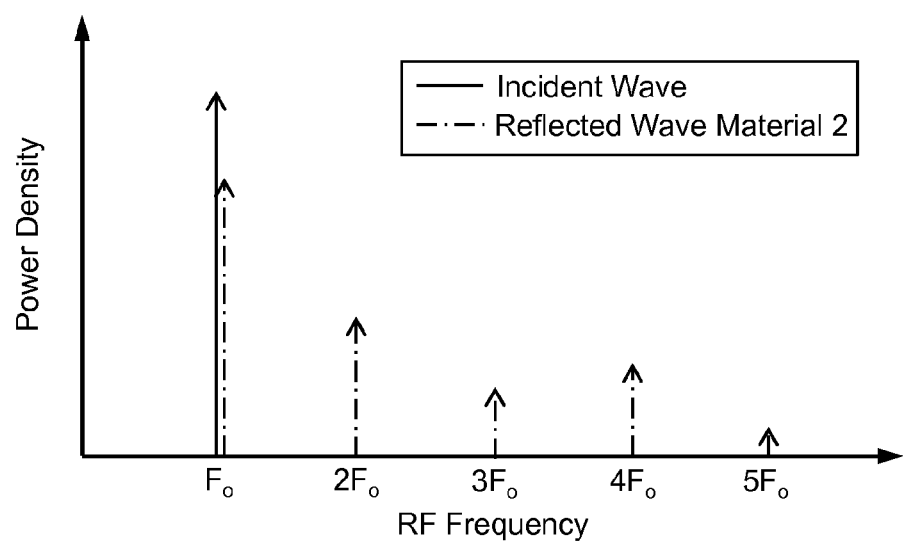
FIG. 4 is the relative amplitude vs. frequency of the incident and reflected electromagnetic waveforms for material #2.

For example, referring now to FIGS. 3-4, Material 1 and Material 2 are radiated at the same fundamental frequency and at the same incident power density. Each generate reflections at the fundamental frequency ($F_o$), double the fundamental frequency ($2F_o$), triple the fundamental frequency ($3F_o$), quadruple the fundamental frequency ($4F_o$), and five times the fundamental frequency ($5F_o$). However, Material 1 is distinguishable from Material 2 because the reflected power density of each harmonic differs between the two materials. For example, the $2F_o$ reflection for Material 1 has a lower power density than the $2F_o$ reflection for Material 2. Similar differentiation exists throughout each of the other harmonic frequencies of the non-linear electromagnetic reflections 124.

This power density pattern of the reflected harmonic frequencies relative to the fundamental frequency is unique to each particular sample material and therefore is indicative of material type. However, it should be noted that different incident power densities produce different patterns of the reflected harmonic frequencies. Therefore, in accordance with various embodiments, the processor 112 controls the system 100, including the high power electromagnetic transmitter 108, to maintain a consistent, known incident power density of the radiated high power electromagnetic radiation 120 at the sample 104. In such embodiments, the known power density allows the processor 112 to properly identify material (e.g., explosives) in the sample 104.

In various embodiments, non-linear electromagnetic reflections 124 are detected in the millimeter wave band of frequencies (generally considered to be between 30-300 GHz). In various embodiments, the non-linear electromagnetic reflections 124 are detected in the terahertz band of frequencies (generally considered to be frequencies between 300 GHz-3 THz). The non-linear electromagnetic reflections 124 will exhibit characteristic harmonic frequencies that correspond to the presence of specific explosive material in the sample 104. In various embodiments, the harmonics are a combination of frequencies from the millimeter wave band and the terahertz band.

The processor 112 provides command and control 128 to the high power electromagnetic transmitter 108 to specify the properties (e.g., frequency(s), bandwidth, duration, duty cycle, magnitude) of the high power electromagnetic radiation 120 radiated to the sample 104. The processor 112 receives digitized responses 132 from the electromagnetic sensor(s) 116. The processor 112, in accordance with various embodiments, collates and catalogs the digitized responses 132 (describing the detected non-linear electromagnetic reflections 124) of an explosive material in the sample 104.

In various embodiments, an operator or a processor (e.g., the processor 112) analyzes the digitized responses 132 to determine the specific characteristics of the non-linear electromagnetic reflections 124. In various embodiments, the system 100 determines the relative power densities of the reflected harmonic frequencies that include a characteristic response associated with an explosive. A particular pattern of reflected harmonic frequencies can be associated with a particular type of explosive material by comparing the non-linear electromagnetic reflections 124 to data stored on the storage device 152 where the stored data correlates known patterns of reflected harmonic frequencies with particular types of explosive material. In accordance with various embodiments, the data stored on the storage device 152 is generated by using the system 100 to detect reflection patterns at various incident power densities for various samples containing one or more known types of explosive material. Thereby, the processor 112 can collate and catalog the data, associating the detected reflection patterns with the known explosive materials at the known incident power densities. When the system 100 is subsequently used on a sample containing an unknown explosive material (or no explosive material), the processor 112 can then compare the detected non-linear electromagnetic reflections 124 to the data stored on the storage device 152 to identify a match between the reflection pattern of the unknown sample and the reflection pattern of a known explosive material.

In various embodiments, the multiple electromagnetic emission sensors 116a, 116b and 116c are each selected to measure specific frequency harmonics of the non-linear electromagnetic reflections 124. Exemplary electromagnetic emission sensors that can be used in embodiments of the system include zero bias diode detectors (e.g., DXP Series gain horn detectors and heterodyne receivers manufactured by Virginia Diodes, Inc. of Charlottesville, Va. and WR Series Gaussian optics (GAO) antennas manufactured by Millitech, Inc. of Northampton, Mass.).

The modules and devices described herein can, for example, utilize the processor 112 to execute computer executable instructions and/or include a processor to execute computer executable instructions (e.g., an encryption processing unit, a field programmable gate array processing unit). It should be understood that the system 100 can include, for example, other modules, devices, and/or processors known in the art and/or varieties of the illustrated modules, devices, and/or processors.

The input device 140 receives information associated with the system 100 (e.g., instructions from a user, instructions from another computing device) from a user (not shown) and/or another computing system (not shown). The input device 140 can include, for example, a keyboard or a scanner. The output device 144 outputs information associated with the system 100 (e.g., information to a printer (not shown), information to an audio speaker (not shown)).

The display device 148 displays information associated with the system 100 (e.g., status information, configuration information). The processor 112 executes the operating system and/or any other computer executable instructions for the system 100 (e.g., sends commands 128 to the high power electromagnetic transmitter 108).

The storage device 152 stores the various information associated with the system 100 and its operation. The storage device 152 can store information and/or any other data associated with the system 100. The storage device 152 can include a plurality of storage devices. The storage device 152 can include, for example, long-term storage (e.g., a hard drive, a tape storage device, flash memory), short-term storage (e.g., a random access memory, a graphics memory), and/or any other type of computer readable storage.

Figure 2:
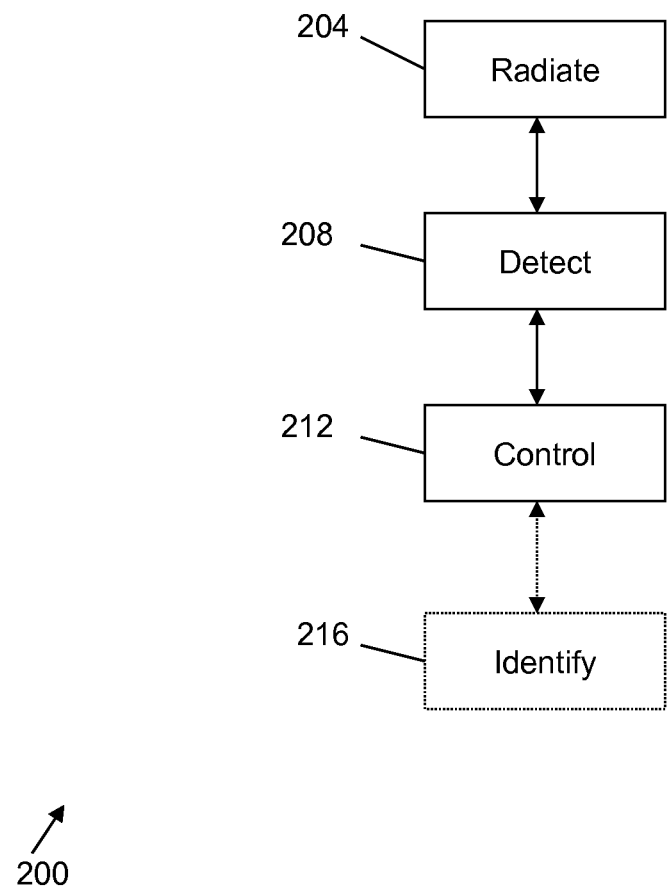
FIG. 2 is a flowchart of a method for detecting explosive materials, according to an illustrative embodiment.

FIG. 2 is a flow diagram illustrating an exemplary method 200 for detecting explosives. The method 200 includes radiating (step 204) a sample with high power electromagnetic radiation using, for example, the high power electromagnetic transmitter 108 of FIG. 1. In various embodiments, the mmW frequencies, W-band frequencies, Ka-band frequencies, or a combination thereof are radiated at the sample.

The method also includes detecting (step 208), using, for example, the electromagnetic sensor 116 of FIG. 1, one or more non-linear electromagnetic reflections having a harmonic frequency corresponding to one or more harmonic frequencies of the radiated high power electromagnetic radiation, wherein the non-linear electromagnetic reflections are reflected by the sample in response to the radiated high power electromagnetic radiation. In various embodiments, the measured reflections include millimeter wave frequencies, terahertz-band frequencies, or a combination of both. In various embodiments, the step of detecting (step 208) includes detecting non-linear electromagnetic radiation reflected by the sample with a plurality of electromagnetic radiation sensors, each of the plurality of electromagnetic sensors (e.g., sensors 116a, 116b, 116c of FIG. 1) configured to measure a specific harmonic frequency.

The method also includes controlling (step 212), by a processor (e.g., processor 112 of FIG. 1), at least one characteristic of the radiated high power electromagnetic radiation. In various embodiments, the processor controls the power of the radiated high power electromagnetic radiation, the frequency of the radiated high power electromagnetic radiation, or both.

The method also includes, in accordance with various embodiments, identifying, by the processor (e.g., processor 112 of FIG. 1), a match between the detected one or more non-linear electromagnetic reflections having a harmonic frequency and one or more harmonic reflections associated with at least one explosive material. In accordance with various embodiments the processor, upon identifying the match, is configured indicate detection of an explosive material. In accordance with various embodiments, the processor is further configured to indicate a type of the detected explosive material. The explosive material type can be determined based on, for example, the relative amplitude pattern of the reflected harmonic frequencies.

The method, in various embodiments, also includes further processing (e.g., collating and cataloging) the reflected harmonic electromagnetic radiation using, for example, the processor 112 of FIG. 1.

An experiment was conducted to detect the presence of Ammonium Nitrate and TNT in two samples. The electromagnetic radiation source (e.g., source 108a of FIG. 1) transmitted W-band radiation (at 95 GHz) to two samples (one containing Ammonium Nitrate and one containing TNT). Multiple sensors were used as harmonic electromagnetic radiation sensors (e.g., sensors 116a and 116b). The first sensor was a model DXP-10-RPFW0 zero bias detector manufactured by Millitech, Inc. in the range of 75-110 GHz. The first sensor measured a signal (e.g., non-linear electromagnetic reflections 124) corresponding to the frequency of the transmitted signal. Other sensors included model DXP-4-RPFW0, WR3.4ZBD, and WR2.2ZBD operating in the frequency ranges 170-260 GHz, 220-335 GHz, and 330-500 GHz, respectively. These sensors were used to detect the reflected $1^{st}$, $2^{nd}$ and $3^{rd}$ harmonic frequencies from the samples. The measured relative levels detected by each sensor was indicative of the presence of ammonia nitrate or TNT in the sample. Samples lacking explosive material (and, specifically lacking Ammonium Nitrate and TNT) tested using the system exhibited significantly different relative peak levels in the reflected harmonic signals. For this test a power density greater than 10 watts/$c^{m2}$ was utilized, sufficient to induce a non-linear response in the sample material.

The above-described systems and methods can be implemented in digital electronic circuitry, in computer hardware, firmware, and/or software. The implementation can be as a computer program product (i.e., a computer program tangibly embodied in an information carrier). The implementation can, for example, be in a machine-readable storage device and/or in a propagated signal, for execution by, or to control the operation of, data processing apparatus. The implementation can, for example, be a programmable processor, a computer, and/or multiple computers.

A computer program can be written in any form of programming language, including compiled and/or interpreted languages, and the computer program can be deployed in any form, including as a stand-alone program or as a subroutine, element, and/or other unit suitable for use in a computing environment. A computer program can be deployed to be executed on one computer or on multiple computers at one site.

Method steps can be performed by one or more programmable processors executing a computer program to perform functions of the invention by operating on input data and generating output. Method steps can also be performed by and an apparatus can be implemented as special purpose logic circuitry. The circuitry can, for example, be a FPGA (field programmable gate array) and/or an ASIC (application-specific integrated circuit). Modules, subroutines, and software agents can refer to portions of the computer program, the processor, the special circuitry, software, and/or hardware that implements that functionality.

Processors suitable for the execution of a computer program include, by way of example, both general and special purpose microprocessors, and any one or more processors of any kind of digital computer. Generally, a processor receives instructions and data from a read-only memory or a random access memory or both. The essential elements of a computer are a processor for executing instructions and one or more memory devices for storing instructions and data. Generally, a computer can include, can be operatively coupled to receive data from and/or transfer data to one or more mass storage devices for storing data (e.g., magnetic, magneto-optical disks, or optical disks).

Data transmission and instructions can also occur over a communications network. Information carriers suitable for embodying computer program instructions and data include all forms of non-volatile memory, including by way of example semiconductor memory devices. The information carriers can, for example, be EPROM, EEPROM, flash memory devices, magnetic disks, internal hard disks, removable disks, magneto-optical disks, CD-ROM, and/or DVD-ROM disks. The processor and the memory can be supplemented by, and/or incorporated in special purpose logic circuitry.

To provide for interaction with a user, the above described techniques can be implemented on a computer having a display device. The display device can, for example, be a cathode ray tube (CRT) and/or a liquid crystal display (LCD) monitor. The interaction with a user can, for example, be a display of information to the user and a keyboard and a pointing device (e.g., a mouse or a trackball) by which the user can provide input to the computer (e.g., interact with a user interface element). Other kinds of devices can be used to provide for interaction with a user. Other devices can, for example, be feedback provided to the user in any form of sensory feedback (e.g., visual feedback, auditory feedback, or tactile feedback). Input from the user can, for example, be received in any form, including acoustic, speech, and/or tactile input.

The above described techniques can be implemented in a distributed computing system that includes a back-end component. The back-end component can, for example, be a data server, a middleware component, and/or an application server. The above described techniques can be implemented in a distributing computing system that includes a front-end component. The front-end component can, for example, be a client computer having a graphical user interface, a Web browser through which a user can interact with an example implementation, and/or other graphical user interfaces for a transmitting device. The components of the system can be interconnected by any form or medium of digital data communication (e.g., a communication network). Examples of communication networks include a local area network (LAN), a wide area network (WAN), the Internet, wired networks, and/or wireless networks.

The system can include clients and servers. A client and a server are generally remote from each other and typically interact through a communication network. The relationship of client and server arises by virtue of computer programs running on the respective computers and having a client-server relationship to each other.

Packet-based networks can include, for example, the Internet, a carrier internet protocol (IP) network (e.g., local area network (LAN), wide area network (WAN), campus area network (CAN), metropolitan area network (MAN), home area network (HAN)), a private IP network, an IP private branch exchange (IPBX), a wireless network (e.g., radio access network (RAN), 802.11 network, 802.16 network, general packet radio service (GPRS) network, HiperLAN), and/or other packet-based networks. Circuit-based networks can include, for example, the public switched telephone network (PSTN), a private branch exchange (PBX), a wireless network (e.g., RAN, bluetooth, code-division multiple access (CDMA) network, time division multiple access (TDMA) network, global system for mobile communications (GSM) network), and/or other circuit-based networks.

The computing device can include, for example, a computer, a computer with a browser device, a telephone, an IP phone, a mobile device (e.g., cellular phone, personal digital assistant (PDA) device, laptop computer, electronic mail device), and/or other communication devices. The browser device includes, for example, a computer (e.g., desktop computer, laptop computer) with a world wide web browser (e.g., Microsoft® Internet Explorer® available from Microsoft Corporation, Mozilla® Firefox available from Mozilla Corporation). The mobile computing device includes, for example, a Blackberry®.

Comprise, include, and/or plural forms of each are open ended and include the listed parts and can include additional parts that are not listed. And/or is open ended and includes one or more of the listed parts and combinations of the listed parts.

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

The invention claimed is:

1. A system for detecting explosive materials, comprising
at least one high power electromagnetic transmitter configured to radiate a sample with high power electromagnetic radiation;
at least one electromagnetic sensor configured to detect one or more non-linear electromagnetic reflections having a harmonic frequency corresponding to one or more harmonic frequencies of the radiated high power electromagnetic radiation, wherein the non-linear electromagnetic reflections are reflected by the sample in response to the radiated high power electromagnetic radiation; and
a processor configured to control the at least one high power electromagnetic transmitter to control at least one characteristic of the radiated high power electromagnetic radiation;
wherein the processor is further configured to process the detected one or more non-linear electromagnetic reflections having a harmonic frequency to identify a match between the detected one or more non-linear electromagnetic reflections having a harmonic frequency and one or more harmonic reflections associated with at least one explosive material by comparing the one or more non-linear electromagnetic reflections with representations, loaded from a memory, of the one or more harmonic reflections associated with at least one explosive material,
wherein the processor, upon identifying the match, is further configured indicate detection of an explosive material,
wherein the processor is further configured to indicate a type of the detected explosive material,
wherein the processor controls the high power electromagnetic transmitter to radiate the high power electromagnetic radiation at a power density level configured to minimize penetration depth of the high power electromagnetic radiation into the sample and cause the high power electromagnetic radiation to reflect off of the sample non-linearly, producing the one or more non-linear electromagnetic reflections having the harmonic frequency corresponding to the one or more harmonic frequencies of the radiated high power electromagnetic radiation, and
wherein the processor further controls the high power electromagnetic transmitter to radiate the high power electromagnetic radiation at the power density level to avoid ignition or detonation of the sample.

2. The system of claim 1, wherein the processor collates and catalogs the detected one or more non-linear electromagnetic reflections having a harmonic frequency reflected by a known explosive material contained by the sample to associate the one or more harmonic reflections with the at least one explosive material.

3. The system of claim 1, wherein the one or more non-linear electromagnetic reflections having a harmonic frequency are caused by a non-linear response to the radiated high power electromagnetic radiation interacting with the sample.

4. The system of claim 1, wherein the high power electromagnetic transmitter radiates the high power electromagnetic radiation at one or more of millimeter wave frequencies, W-band frequencies, or Ka-band frequencies.

5. The system of claim 1, wherein the high power electromagnetic transmitter radiates the high power electromagnetic radiation at a power density of at least 10 Watts/cm$^2$.

6. The system of claim 1, wherein millimeter wave frequencies, terahertz-band frequencies, or a combination of both are detected by the at least one electromagnetic sensor.

7. The system of claim 1, wherein each of a plurality of the electromagnetic sensors is configured to detect any of the one or more non-linear electromagnetic reflections having a specific harmonic frequency of the radiated high power electromagnetic radiation.

8. The system of claim 1, wherein the processor is configured to identify the match between the detected one or more non-linear electromagnetic reflections having the harmonic frequency and the reflective harmonic characteristics of the at least one explosive material by comparing a relative amplitude of the detected one or more non-linear electromagnetic reflections having the harmonic frequency with a relative amplitude of the one or more harmonic reflections associated with the at least one explosive material.

9. The system of claim 1, wherein the type of the detected explosive material is at least one of HMX, Trinitrotoluene (TNT), C-4, Semtex, or Ammonium Nitrate.

10. A method for detecting explosive materials, the method comprising:
radiating a sample with high power electromagnetic radiation using at least one high power electromagnetic transmitter;
detecting, using one or more electromagnetic sensors, one or more non-linear electromagnetic reflections having a harmonic frequency corresponding to one or more harmonic frequencies of the radiated high power electromagnetic radiation, wherein the non-linear electromagnetic reflections are reflected by the sample in response to the radiated high power electromagnetic radiation;
controlling, by a processor, the at least one high power electromagnetic transmitter to control at least one characteristic of the radiated high power electromagnetic radiation and to radiate the high power electromagnetic radiation at a power density level configured to minimize penetration depth of the high power electromagnetic radiation into the sample and cause the high power electromagnetic radiation to reflect off of the sample non-linearly, producing the one or more non-linear electromagnetic reflections having the harmonic frequency corresponding to the one or more harmonic frequencies of the radiated high power electromagnetic radiation, where the power density level is configured to avoid ignition or detonation of the sample;
identifying, by the processor, a match between the detected one or more non-linear electromagnetic reflections having a harmonic frequency and one or more harmonic reflections associated with at least one explosive material by comparing the one or more non-linear electromagnetic reflections with representations, loaded from a memory, of the one or more harmonic reflections associated with at least one explosive material;
indicating, upon identifying the match, detection of an explosive material and a type of the detected explosive material.

11. The method of claim 10, further comprising collating and cataloging, on the processor, the detected one or more non-linear electromagnetic reflections having a harmonic frequency reflected by a known explosive material contained by the sample to associate the one or more harmonic reflections with the at least one explosive material.

12. The method of claim 10, further comprising radiating, by the high power electromagnetic transmitter, one or more of millimeter wave frequencies, W-band frequencies, or Ka-band frequencies.

13. The method of claim 10, further comprising detecting, by the at least one electromagnetic sensor, millimeter wave frequencies, terahertz-band frequencies, or both.

14. The method of claim 10, wherein the step of identifying is performed by comparing a relative amplitude of the detected one or more non-linear electromagnetic reflections having the harmonic frequency with a relative amplitude of the one or more harmonic reflections associated with the at least one explosive material.

15. The method of claim 14, further comprising detecting, by each of a plurality of the electromagnetic sensors, any of the one or more non-linear electromagnetic reflections having a specific harmonic frequency of the radiated high power electromagnetic radiation.

16. The method of claim 10 wherein the step of controlling, by a processor, at least one characteristic of the radiated high power electromagnetic radiation is performed by controlling at least one of a power of the radiated high power electromagnetic radiation or a frequency of the radiated high power electromagnetic radiation.

* * * * *